(12) United States Patent
Govindasamy et al.

(10) Patent No.: US 10,542,743 B2
(45) Date of Patent: Jan. 28, 2020

(54) ISOLATION, EXPANSION AND CHARACTERIZATION OF WHARTON'S JELLY MESENCHYMAL STEM CELLS

(71) Applicant: HYGIEIA THERAPEUTICS SDN BHD, Putrajaya (MY)

(72) Inventors: Vijayendran Govindasamy, Putrajaya (MY); Wijenthiran Kunasekaran, Putrajaya (MY); Naresh Waran Gnanasegaran, Putrajaya (MY)

(73) Assignee: HYGIEIA THERAPEUTICS SDN BHD, Putrajaya (MY)

( * ) Notice: Subject to any disclaimer, the term of this patent is extended or adjusted under 35 U.S.C. 154(b) by 310 days.

(21) Appl. No.: 14/987,666

(22) Filed: Jan. 4, 2016

(65) Prior Publication Data
US 2016/0194609 A1  Jul. 7, 2016

(30) Foreign Application Priority Data

Jan. 5, 2015  (MY) .......................... PI 2015000025

(51) Int. Cl.
| | | |
|---|---|---|
| *C12N 5/0775* | (2010.01) | |
| *A01N 1/02* | (2006.01) | |
| *C12N 5/073* | (2010.01) | |
| *A61K 35/51* | (2015.01) | |

(52) U.S. Cl.
CPC ............ *A01N 1/0221* (2013.01); *A61K 35/51* (2013.01); *C12N 5/0605* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 5,919,702 A | 6/1999 | Purchio et al. | |
| 2005/0148074 A1 | 7/2005 | Davies et al. | |
| 2006/0223177 A1* | 10/2006 | Harris ................... | C12N 5/0607 435/325 |
| 2007/0190042 A1* | 8/2007 | Edinger ................ | C12N 5/0605 424/94.63 |
| 2007/0224658 A1* | 9/2007 | Halbert ................. | C12N 5/0018 435/29 |
| 2009/0142839 A1* | 6/2009 | Primiano ............. | C12N 5/0606 435/455 |
| 2011/0312091 A1* | 12/2011 | Zhao .................... | C12N 5/0605 435/368 |

FOREIGN PATENT DOCUMENTS

| | | | |
|---|---|---|---|
| WO | WO 2011/101834 | * | 8/2011 |
| WO | 2012/131618 A1 | | 10/2012 |

OTHER PUBLICATIONS

Nekanti et al., "Optimization and scale-up of Wharton's jelly-derived mesenchymal stem cells for clinical applications", Stem Cell Research, 2010, vol. 5, pp. 244-254. (Year: 2010).*
Allcells, HTTPS://www.ALLCELLS.com/blog/how-to-passage-and-subculture-mesenchymal-stem-cells/, "How to Passage and Subculture-Mesenchymal Stem Cells", Mar. 1, 2013, pp. 1-8.*
C.C. Yang et al, in Plos One, vol. 3, doi: 10.1371/journal.pone.0003336 "Transplantation of Human Umbilical Mesenchymal Stem Cells from Wharton's Jelly after Complete Transection of the Rat Spinal Cord" (2008).
C. Y. Fong et al, in Stem Cell Reviews, "Human Wharton's Jelly Stem Cells Have Unique Transcriptome Profiles Compared to Human Embryonic Stem Cells and Other Mesenchymal Stem Cells" vol. 7, pp. 1 to 16 (2011).
McGuirk and Weiss, in Placenta, vol. 32, pp. S304-S310 "Promising cellular therapeutics for prevention or management of graft-versus-host disease (a review)" (2011).
Pal R, Hanwate M, Jan M, et al. Journal of Tissue Engineering and Regenerative Medicine "Phenotypic and functional comparison of optimum culture conditions for upscaling of bone marrow-derived mesenchymal stem cells" 2009; 3:163-74.

* cited by examiner

*Primary Examiner* — Laura Schuberg
(74) *Attorney, Agent, or Firm* — Maschoff Brennan (57) ABSTRACT

The present invention relates to a method of isolating mesenchymal stem cells originated from Wharton's jelly (WJ-MSC) from single donor. The method for isolating and proliferating viable cells from Wharton's jelly wherein the method includes the steps of (a) obtaining umbilical cord tissue comprising of viable cells from Wharton's jelly, (b) isolating the viable cells in a sample collection media, (c) preparing a primary stock culture using the viable cells from step (b), (d) proliferating the primary stock culture from step (c) to obtain sub-cultured stocks, (e) harvesting the viable cells from the sub-cultured stocks from step (d) and (f) cryo-preserving the viable cells from step (e) under cryogenic conditions.

3 Claims, 6 Drawing Sheets
(5 of 6 Drawing Sheet(s) Filed in Color)

ISOLATION, EXPANSION AND CHARACTERIZATION OF WHARTON'S JELLY MESENCHYMAL STEM CELLS

FIELD OF TECHNOLOGY

The present invention relates to methods of isolating mesenchymal stem cells originated from Wharton's jelly (WJ-MSC) from single donor. In addition, the present disclosure also relates to sample collection media and expansion media used in these methods as well as characterization of mesenchymal stem cells and their use in the treatment of various disorders.

BACKGROUND OF TECHNOLOGY

Stem cells (SCs) have been widely characterized as precursors that self-replicate with the ability to give rise to one or more cell types, known as potency. Stem cells can be hierarchically classified as unipotent, multipotent, pluripotent and totipotent. Unipotent stem cells can produce only one cell type (e.g. neurons), whereas multipotent ones can differentiate into several cell types (e.g. hematopoietic stem cells, HSCs). An embryonic stem cell (ESC), derived from the inner cell mass (ICM) of the embryo is pluripotent as it can differentiate into cells of three germ layers, but not into trophoblastic cells, whereas the zygote is totipotent as it produces cells of embryonic as well as extra-embryonic tissue. On the other hand, SCs also can be isolated from a variety of adult tissues sources such as bone marrow, skin, adipose tissues and many more. However, these sources pose limitations which include lack of starting material, invasive procurement procedures, tedious processing techniques and most importantly, limited proliferative capacity due to their adult origin.

Another source originating from extra-embryonic tissue is Wharton's jelly (WJ) of human umbilical cord which has gained popularity due to its non-controversial source and abundance in mesenchymal stem cells (MSC) population from its raw starting material as disclosed by McGuirk and Weiss, in Placenta, vol. 32, pages S304-10 (2011). Further, WJ-MSCs share many properties with adult mesenchymal stem cells originated from bone marrow (BM-MSCs), but are generally considered as a more primitive population than the latter. In fact, while they possess several characteristics of ESCs, they do not form teratomas upon transplantation and their research does not raise ethical or legal issues. All these features open attractive perspectives for the propagation and engineering of WJ-MSCs for cell-based therapies.

In addition, they are also relatively easy to harvest and to process as compared to bone marrow or embryonic origin prior to ex vivo expansion as testified by C. C. Yang et al, in Plos One, vol. 3, doi: 10.1371/journal.pone.0003336 (2008). Another advantage of this source is that these cells have high proliferation rates, wide multi-potency, hypo-immunogenicity, do not induce tumorigenesis and have anti-tumor properties as claimed by C. Y. Fong et al, in Stem Cell Reviews, vol. 7, pages 1 to 16 (2011).

The potential of WJ-MSC was comprehensively investigated in which exposure towards exogeneous growth factors has shown to contribute to the formation of pre-chodrocytes cells as described in U.S. Pat. No. 5,919,702 by Purchio et al. Further work to obtain enriched osteoprogenitor cells from Wharton's Jelly was conducted by Davies et al., in their U.S. Patent application 2005/0148074. Recently, Majumdar in WO2012131618 A1 has described the method of obtaining pooled WJ-MSCs for the purpose of producing an off-the-shelf product. This was meant to serve as allogeneic MSC product for therapeutics application in large scale. Though the idea is noteworthy, it should also be noted that genetic variability among donors is a confounding factor that requires serious attention.

Though the allogeneic MSC that are being used in the transplantation have been thoroughly checked for human leukocyte antigen (HLA) markers, any variation especially in terms of genetic that may occur during the course of transplantation would be very difficult to identify and subsequently control. In addition, having a pooled cell culture has another disadvantage as it might contribute to graft versus host disease in certain recipients thus requiring rigorous follow-up sessions which would be unnecessary if the cells were to have propagated from a single donor. On the other hand, among the benefits of using cells isolated from single donor are reduced disease transmission, reduced alloimmunization and superior function and storage characteristics.

Taking into consideration of all these hurdles, the present disclosure relates to a composition comprising of large scale expansion of WJ-MSC from a single donor for the purpose of allogeneic transplantation.

SUMMARY OF THE INVENTION

The present invention relates to a method of isolating mesenchymal stem cells originating from Wharton's jelly (WJ-MSC) from at least a single donor. The method for isolating and proliferating viable cells from Wharton's jelly is described herein, wherein the method includes the steps of (a) obtaining umbilical cord tissue comprising of viable cells from Wharton's jelly, (b) isolating the viable cells in a sample collection media, (c) preparing a primary stock culture using the viable cells from step (b), (d) proliferating the primary stock culture from step (c) to obtain sub-cultured stocks, (e) harvesting the viable cells from the sub-cultured stocks from step (d) and (f) cryo-preserving the viable cells from step (e) under cryogenic conditions. The present invention also discloses the sample collection media and expansion media used in the method. The present invention also discloses the characterization of the mesenchymal stem cells isolated from Wharton's jelly and their use in treating various diseases.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

In view of the potential application of stem cells from Wharton's jelly for clinical medicine, there is growing interest in optimizing their expansion protocols so as to produce large quantities of cells for therapeutic applications, which is cost-effective and yet maintains their phenotype and functional capabilities. To date, there is inconsistency among laboratories concerning the isolation process example of using pooled samples. The present invention, overcomes the inconsistency by setting optimal culture conditions for effective clinical-grade production of large number of stem cells from Wharton's jelly in a short time, economizing on cost and time to serve for better cellular therapy. The results of the study are highly reproducible and consistent, making them useful for in vivo as well as in vitro manipulation without the stem cells from Wharton's jelly losing their vigour and chromosomal stability.

Example 1

Isolation of Wharton's Jelly Mesenchymal Stem Cells

Cleaning Process

Upon receiving the umbilical cord from the hospital (within 48 hours post-delivery), the umbilical cord was cut into three pieces, approximately 4-5 cm long and individual segmented cord was washed three times in 30 mL of ddH$_2$O in a 50 mL centrifuge tube to remove blood contaminant. Next, the clean cord was immersed in a 50 mL centrifuge tube containing 30 ml of Dulbecco's Phosphate Buffered Saline (DPBS), 20% Antibiotic-Antimycotic (1×) and 20% Penicillin-Streptomycin (1×). This process was repeated three times to disinfect the cord. The cord need to be stored at +4° C. until processing (within 24 hours) or can be processed immediately.

Isolation Process (Culture 0)

The isolation process was carried out in Biological Safety Cabinet (BSC) at a current good manufacturing practise facility with the following parameters.

| SI No. | Parameters | Range |
|---|---|---|
| 1 | Temperature | 37° C. ± 0.5 |
| 2 | Carbon Dioxide range | 5% ± 0.5 |
| 3 | Room Temperature | 18° C. ± 2.0 |
| 4 | Relative Humidity (RH) | 55% ± 5 |
| 5 | Differential Pressure (PA) | 10 ± 10 |

Prior to the isolation process, sterilization by means of wiping the BSC surface with 70% Isopropyl Alcohol (IPA) using sterile wipes need to be done as well as UV sterilization for 30 minutes. Tubes containing the cord were transferred into the BSC. The cords were then washed three times in three different units of 50 mL centrifuge tube containing 30 mL of ddH$_2$O, 1% Antibiotic-Antimycotic (1×) and 1% Penicillin-Streptomycin (1×) with additional heparin injection into the blood vessels to remove blood clot. By using sterile scissor (sharp/sharp), scalpel, blade and forceps, the cord was manipulated in a sterile surgical tray or culture plate. Blood vessels were then removed from each piece by incising the cord lengthwise using sterile scissor (sharp/sharp), blade and forceps. Next the cords were immersed into 70% ethanol for 30 seconds for further disinfection process before immediate immersion into ddH$_2$O 3 times for 30 seconds per dip to completely remove the traces of 70% ethanol. The cords were transferred into new three units of 50 mL centrifuge tube containing DPBS and 5% Antibiotic-Antimycotic (1×) and incubated at 37° C. overnight. On the next day, the cords were then washed with DPBS three times with 2 minutes incubation. Each cord tissue was transferred into three new 50 mL centrifuge tubes containing 15 mL solution mixture of 4 mg/mL Collagenase Type-IV dissolved in Knockout-Dulbecco's Modified Eagle Medium (KO-DMEM). The cord tissues were later minced using sterile scissor (sharp/sharp) until it becomes tiny pieces ($\approx$2 mm$^3$) and incubated at 37° C. in shaking incubator for overnight.

2 mL of 0.05% Trypsin-EDTA was added the next day to the digested tissue and incubated for 10 minutes. Next, equal volume of neutralization medium containing 95% KO-DMEM and 5% FBS was added into each tube to neutralize the activity of Collagenase Type-IV. The mixture was then centrifuged at 1800 rpm for 5 minutes at room temperature (18° C.±2° C.).

Upon centrifugation, the top aqueous phase of the mixture (approximately 0.3 cm above the pale yellow phase) was slowly removed using a pipette. Further, the jelly like solution (containing dissociated cord pieces) was strained using 100 μm cell strainer into new three units of 50 mL centrifuge tube and centrifuged at 1800 rpm for 5 minutes after adding equal volume of complete culture medium (CCM)[#]

[#]Media Composition for Wharton Jelly Complete Culture Medium (CCM)

| Sr. No. | Media Components | Concentration | Component Composition | Example in a 50 mL |
|---|---|---|---|---|
| 1 | DMEM-KO media* | 1 unit | 73% | 35.5 mL |
| 2 | Fetal Bovine Serum* | 10 units | 20% | 5.0 mL |
| 3 | Penicillin/Streptomycin* | 200 units mL$^{-1}$/ 200 μg mL$^{-1}$ | 5% | 1.0 mL |
| 4 | Antibiotic-Antimycotic | 10,000 units/mL 25 μg/mL of Fungizone | 5% | 1.0 mL |
| 5 | Glutamax* | 1 units | 2% | 1.0 mL |

*commercially available reagents

The supernatant was then discarded and re-suspended with 5 mL of CCM. Upon cell count, the cell suspension was cultured in three units of T25 cm$^2$ flask at 37° C. in 5% humidified CO$_2$ incubator and keep the flasks undisturbed for 24 hours. After 24 hours, the flasks were transferred from 5% humidified CO$_2$ incubator to the BSC. Next the conditioned media was discarded and replaced with 5 mL of CCM before transferring them back to CO$_2$ incubator. The cells were observed under inverted microscope every 2 days until the cells reach 80%±5% confluency. At day 7, the flasks were transferred from 5% humidified CO$_2$ incubator to the BSC. 5 mL of CCM was added into the flask and transferred back to CO$_2$ incubator. The same step was repeated at Day 14. Upon reaching 85%±5% confluency, cells were then sub-cultured to Subculture Cell Stock 1.

Example 2

Expansion of Wharton's Jelly Stem Cells (WJ-MSCs) from Culture Cell 0 to Subculture Cell Stock 1

Prior to work, BSC need to be cleaned via UV sterilization for 30 minutes and also with sterile 70% Isopropyl Alcohol (IPA) and sterile wipes. The T25 cm² culture flasks containing Subculture Cell Stock 0 (SC0) cells were transferred into cleaned and sterilized BSC. A total of 5 mL of Dulbecco's Phosphate Buffered Saline (DPBS) was used for rinsing upon removing all conditioned medium from culture flasks via serological pipettes.

| Sr. No. | Type of Tissue Culture Vessel | Amount of DPBS per rinse (mL) |
|---|---|---|
| 1 | T25 cm² Culture Flask | 5 |

The flasks were left for 1 minute and the DPBS was discarded into a waste beaker and later added with 1 mL of 0.05% Trypsin-EDTA into each flask and incubated at 37° C. in 5% humidified $CO_2$ incubator for less than 10 minutes.

| Sr. No. | Type of Tissue Culture Vessel | Amount of 0.05% Trypsin-EDTA (mL) |
|---|---|---|
| 1 | T25 cm² Culture Flask | 1 |

Cells were observed under inverted microscope for round and floating cells to confirm complete cell detachment. Then, Complete Culture Media (CCM) was added to neutralize 0.05% Trypsin-EDTA activity.

| Sr. No. | Type of Tissue Culture Vessel | Amount of CCM (mL) |
|---|---|---|
| 1 | T25 cm² Culture Flask | 4 |

Cell suspension was transferred into a new 50 mL centrifuge tube and centrifuged at 1500 rpm for 10 minutes at room temperature (18° C.±2° C.). The supernatant was discarded into waste beaker and 20 mL of CCM was added into the tube to re-suspend the pellet. After performing cell count, the cells were cultured into T75 cm² culture flasks for Subculture Cell Stock 1 (SC1) culture.

| Sr. No. | Type of Tissue Culture Vessel | Seeding Density |
|---|---|---|
| 1 | T75 cm² Culture Flask | $0.2 \times 10^6$ cells |

After adding up to 10 mL of CCM into the flasks, they were then incubated at 37° C. in 5% humidified $CO_2$ incubator. The cells were observed under inverted microscope every 2 days until the cells reach 80%±5% confluency. At day 7, the flasks were transferred from 5% humidified $CO_2$ incubator to the BSC. 5 mL of CCM was added into the flask and transferred back to $CO_2$ incubator. The same step was repeated at Day 14. Upon reaching 85%±5% confluency, cells were then sub-cultured to Subculture Cell Stock 2.

Example 3

Expansion of Wharton's Jelly Stem Cells from Subculture Cell Stock 1 to Subculture Cell Stock 2

Prior to work, BSC need to be cleaned via UV sterilization for 30 minutes and also with sterile 70% Isopropyl Alcohol (IPA) and sterile wipes. The T25 cm² culture flasks containing Subculture Cell Stock 1 (SC1) cells were transferred into cleaned and sterilized BSC. A total of 5 mL of Dulbecco's Phosphate Buffered Saline (DPBS) was used for rinsing upon removing all conditioned medium from culture flasks via serological pipettes.

| Sr. No. | Type of Tissue Culture Vessel | Amount of DPBS per rinse (mL) |
|---|---|---|
| 1 | T25 cm² Culture Flask | 5 |

The flasks were left for 1 minute and the DPBS was discarded into a waste beaker and later added with 1 mL of 0.05% Trypsin-EDTA into each flask and incubated at 37° C. in 5% humidified $CO_2$ incubator for less than 10 minutes.

| Sr. No. | Type of Tissue Culture Vessel | Amount of 0.05% Trypsin-EDTA (mL) |
|---|---|---|
| 1 | T25 cm² Culture Flask | 1 |

Cells were observed under inverted microscope for round and floating cells to confirm complete cells detachment. Then, Complete Culture Media (CCM) was added to neutralize 0.05% Trypsin-EDTA activity.

| Sr. No. | Type of Tissue Culture Vessel | Amount of CCM (mL) |
|---|---|---|
| 1 | T25 cm² Culture Flask | 4 |

Cell suspension was transferred into a new 50 mL centrifuge tube and centrifuged at 1500 rpm for 10 minutes at room temperature (18° C.±2° C.). The supernatant was discarded into waste beaker and 20 mL of CCM was added into the tube to re-suspend the pellet. After performing cell count, the cells were cultured into T75 cm² culture flasks for Subculture Cell Stock 2 (SC2) culture.

| Sr. No. | Type of Tissue Culture Vessel | Seeding Density |
|---|---|---|
| 1 | T75 cm² Culture Flask | $0.2 \times 10^6$ cells |

After adding up to 10 mL of CCM into the flasks, they were then incubated at 37° C. in 5% humidified $CO_2$ incubator. The cells were observed under inverted microscope every 2 days until the cells reach 80%±5% confluency. At day 7, the flasks were transferred from 5% humidified $CO_2$ incubator to the BSC. 5 mL of CCM was added into the flask and transferred back to $CO_2$ incubator. The same step was repeated at Day 14. Upon reaching 85%±5% confluency, cells were then sub-cultured to Subculture Cell Stock 2.

Example 4

Harvest and Cryopreservation of Wharton's Jelly Stem Cells at Subculture Cell Stock Harvest of WJ-MSCs at SC2

Prior to work, BSC need to be cleaned via UV sterilization for 30 minutes and also with sterile 70% Isopropyl Alcohol (IPA) and sterile wipes. The culture flasks containing Subculture Cell Stock 1 (SC1) cells were transferred into cleaned and sterilized BSC. Routine rinsing step was repeated twice using volume of Dulbecco's Phosphate Buffered Saline (DPBS) as shown in the table below, upon removing all conditioned medium from culture flasks via serological pipettes.

| Sr. No. | Type of Tissue Culture Vessel | Amount of DPBS per rinse (mL) |
|---|---|---|
| 1 | 1 Chamber Cell Stack | 50 |
| 2 | 5 Chamber Cell Stack | 250 |

The flasks were left for 1 minute and the DPBS was discarded into a waste beaker and later added with 0.05% Trypsin-EDTA into each flask and incubated at 37° C. in 5% humidified $CO_2$ incubator for less than 10 minutes.

| Sr. No. | Type of Tissue Culture Vessel | Amount of 0.05% Trypsin-EDTA (mL) |
|---|---|---|
| 1 | 1 Chamber Cell Stack | 20 |
| 2 | 5 Chamber Cell Stack | 100 |

Cells were observed under inverted microscope for round and floating cells to confirm complete cells detachment. Then, Complete Culture Media (CCM) was added to neutralize 0.05% Trypsin-EDTA activity.

| Sr. No. | Type of Tissue Culture Vessel | Amount of CCM (mL) |
|---|---|---|
| 1 | 1 Chamber Cell Stack | 80 |
| 2 | 5 Chamber Cell Stack | 400 |

Cell suspension was transferred into a new 250 mL centrifuge tube and centrifuged at 1800 rpm for 10 minutes at room temperature (18° C.±2° C.). The supernatant was discarded into waste beaker and 20 mL of CCM was added into the tube to re-suspend the pellet. The cells suspension was then pooled into one single 250 mL centrifuge tube. After performing cell count, the cells were then proceeded with "Retention Cells" and "Freezing Cells in Cryobag" steps. The cell suspension was split as follows:

| Sr. No. | Label Tubes | Amount of Cells |
|---|---|---|
| 1 | Retention Cells | 50 × 10$^6$ cells |
| 2 | Freezing Cells in Cryobag | 60 × 10$^6$ cells |

Example 5

Cryopreservation of WJ-MSCs Subculture Cell Stock 2 as Finished Product

Prior to work, BSC need to be cleaned via UV sterilization for 30 minutes and also with sterile 70% Isopropyl Alcohol (IPA) and sterile wipes. An appropriate volume of Cell Freezing Medium (CFM), with a mixture of Fetal Bovine Serum (FBS) and Dimethyl Sulfoxide (DMSO) need to be prepared at a ratio shown in the table below:

| Sr. No. | Media Components | Component Composition | 50 mL |
|---|---|---|---|
| 1 | Fetal bovine serum (FBS) | 90% | 45 mL |
| 2 | Dimethyl Sulfoxide (DMSO) | 10% | 5 mL |

The mixture was then carefully mixed using 10 mL pipette with avoidance of bubbles formation. The tube cap needs to be tightened and wrapped with aluminium foil to protect from light. It was kept in +4° C. prior to use.

Cells from "retention cells" were centrifuged at 1500 rpm for 10 minutes at room temperature (18° C.±2° C.). The supernatant was then discarded and the pellet was re-suspended with 5 mL of the freshly prepared CFM. A total of 1 mL of CFM was transferred containing approximately 10×10$^6$ cells into each of five units labelled 1.8 mL cryogenic vials.

A 30 mL cryobag was wiped with sterile 70% IPA and transferred into the BSC. Air was fully removed to make it air-tight using a 30 mL syringe and 22 G syringe needle to avoid bubble formation during the load of the cells into the bag. Cells from 'Freezing cells in Cryobag' were centrifuged at 1500 rpm for 10 minutes at room temperature (18° C.±2° C.). The supernatant was then discarded and the pellet was re-suspended with 30 mL of the freshly prepared CFM. By using a 30 mL syringe, the cell suspension containing approximately 60×10$^6$ cells was loaded into a 30 mL cryobag. The cryobag was then sealed using sealer while the excess tubes were removed. Cryobags were then placed in cassettes before transferring them into −80° C. freezer for 24 to 48 hours. The cryobags were placed into a frame located in vapour phase of liquid nitrogen ($LN_2$) storage freezer.

Example 6

Figure 1:
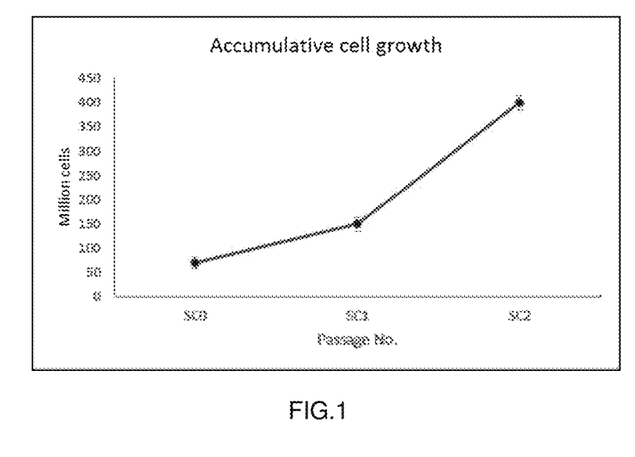
FIG. 1 illustrates the accumulative cell growth of Wharton's Jelly mesenchymal stem cells.
Figure 2:
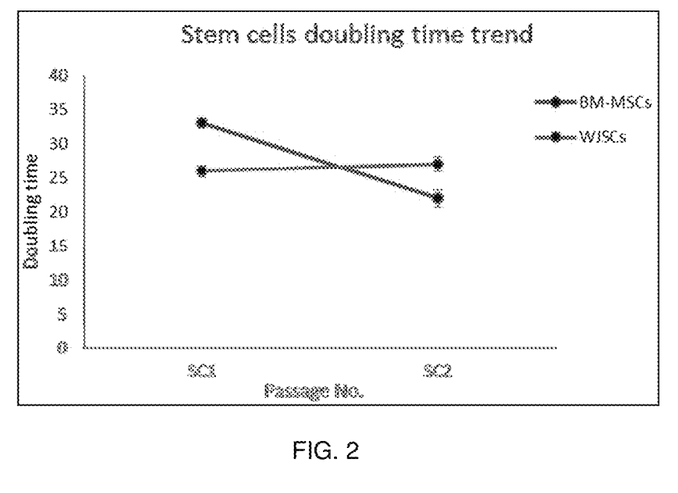
FIG. 2 illustrates the population doubling time for Wharton's Jelly mesenchymal stem cells and BM-MSCs.

Growth Kinetics Study of WJ-MSCs at Subculture 2 which is Also Known as Finish Product The proliferation rate was determined by plating 5000 cells/cm2 from WJ-MSCs and BM-MSCs (control cell lines) per T25 cm$^2$ culture flask (BD Pharmingen, San Diego, Calif.). Three replicates were performed for each passage and time point. Cells were detached by trypsinization after reaching confluency of 90%. Cells were counted and assessed for viability by means of trypan blue dye exclusion before the next passage. Cells were replated for subsequent passages, and total of 2 passages were studied in this experiment. Growth kinetics was analysed by calculating population doubling (PD) time. The PD time was obtained using the formula:

$$PD = t\,plg2/(lgNH - lgNI),$$

wherein NI is the inoculum cell number, NH is the cell harvest number, and t is the time of the culture (in hours). The population doubling trend in WJMSCs is illustrated in FIG. 1. The WJ-MSCs showed a stable PD time throughout passage 1 to 2 which were within the range of 26 to 28 hours meanwhile rapid decrease in PD time for BM-MSCs were observed on the same passage (refer FIG. 2).

Example 7

Figure 3:
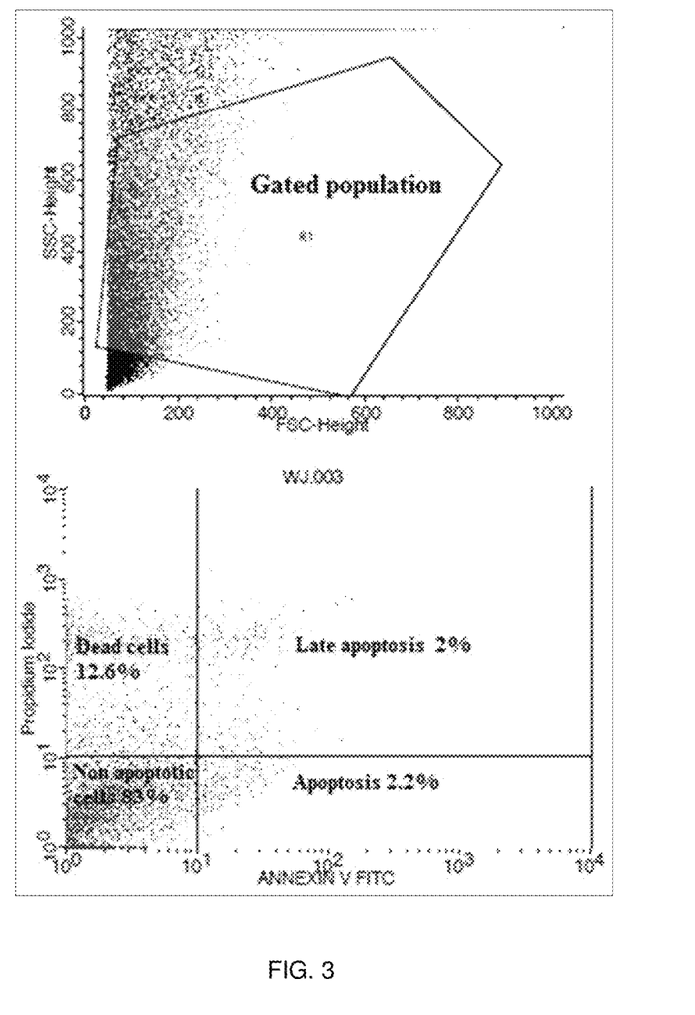
FIG. 3 illustrates the detection of percentage of apoptosis in WJ-MSCs using Annexin V/propidum iodide.

Cell Apoptosis Study of WJ-MSCs at Subculture 2 which is Also Known as Finish Product For Annexin V/propidium iodide (PI) assays (refer FIG. 3), the WJMSCs cells at passage 2 (finish product) were stained with Annexin V-FITC and PI and then evaluated for apoptosis by flow cytometry according to the manufacturer's protocol (Invitrogen). Briefly, $1\times10^6$ cells were washed twice with cold PBS and stained with 5 µL of Annexin V-FITC and 8 µL of PI (5 µg/mL) in 1× binding buffer [10 mmol/L HEPES (pH 7.4), 140 mmol/L NaOH, and 2.5 mmol/L $CaCl_2$] for 10 min at room temperature in the dark. The apoptotic cells were determined using a Becton Dickinson FACSCalibur cytofluorometer. Both early apoptotic (Annexin V-positive and PI-negative) and late apoptotic (Annexin V-positive and PI-positive) cells were included in cell death determinations. It was shown that more 83% of the cryopreserved cells at sub-culture 2 (finish product) are viable and non-apoptotic cells. Only a small percentage of cells were observed in the apoptosis category (apoptosis: 2.2% and late apoptosis 2%). The rest of the population were dead which commonly occurred during sample preservation.

Example 8

Figure 4:
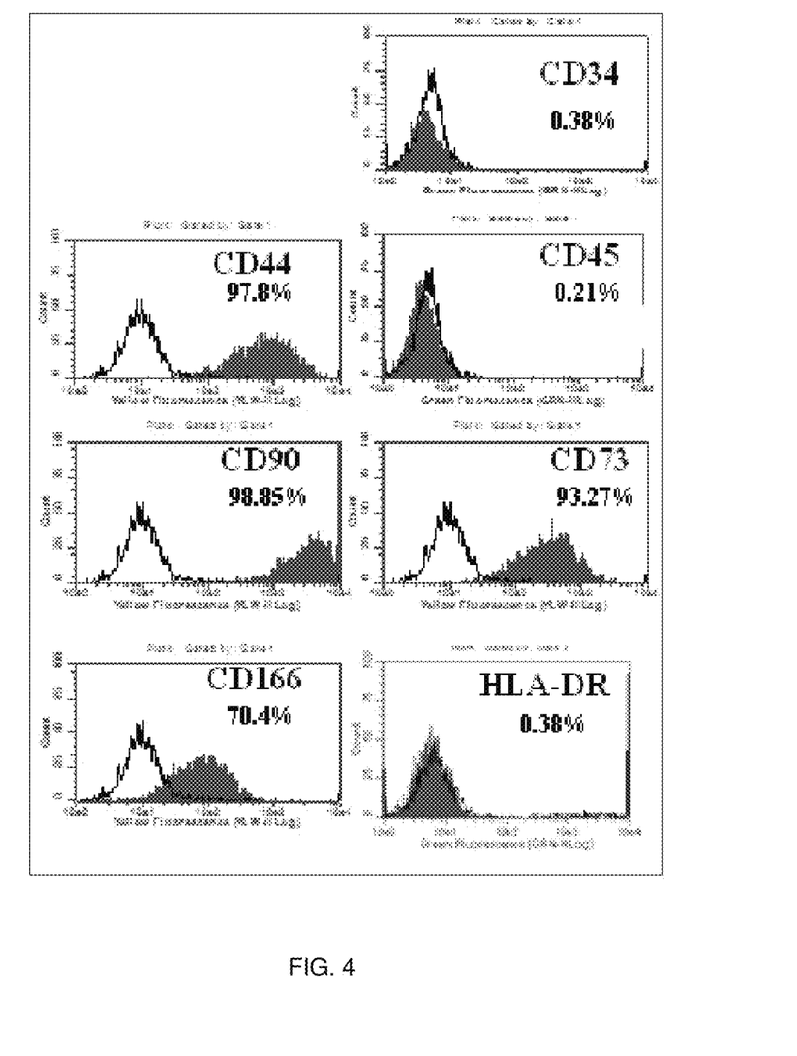
FIG. 4 illustrates immunophenotyping for MSC markers for WJ-MSCs at SC2.

Cell Surface Antigen Study of WJ-MSCs at Subculture 2 which is Also Known as Finish Product The immunophenotyping was done by using flow cytometry at passage 2 (finish product). On reaching 90% confluency, the cells were harvested with 0.05% trypsin (Invitrogen) and resuspended in phosphate buffered saline (DPBS) at a cell density of $1.5\times10^6$ cells/mL. Two hundred microliters of the cell suspension ($1\times10^5$ cells) was incubated with the labelled antibodies in the dark for 1 hour at 37° C. The following antibodies were used to mark the cell surface epitopes: CD90-phycoerythrin (PE), CD44-PE, CD73-PE, CD166-PE and CD34-PE, CD45-fluoroisothiocyanate (FITC), and HLA-DR-FITC (all from BD Pharmingen). All analyses were standardized against negative control cells incubated with isotype-specific immunoglobulin (Ig) G1-PE and IgG1-FITC (BD Pharmingen). Immunophenotyping of stem cells derived from WJSCs showed that the cells were negative for hematopoietic markers CD34 and CD45 and HLA-DR, whereas more than 90% of cells were positive for mesenchymal stem cell markers CD44, CD73, CD90, and 70.4% for CD166 (refer FIG. 4).

Example 9

Figure 5:
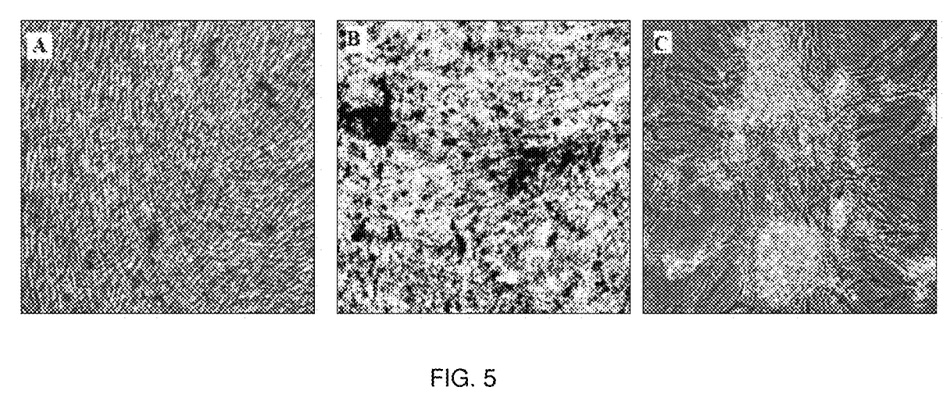
FIG. 5 illustrates the adipogenic (A), osteogenic (B) and chondrogenic (C) differentiation of WJMSCs.

Tri-Lineage Differentiation of WJ-MSCs at Subculture 2 which is Also Known as Finished Product The cultures were initiated at a density of 1000 cells/cm$^2$ in 6-well plates and were grown to confluence and subjected to differentiation into adipogenic, chondrogenic, and osteogenic lineages as per the method described earlier (Pal R, Hanwate M, Jan M, et al. J Tissue Eng Regen Med 2009; 3:163-74.). Adipogenic lineage was stimulated by inducing the cells with 10% FBS, 200 mmol/L indomethacin, 0.5 mmol/L 3-isobutyl-1-methyxanthine (IBMX), 10 mg/mL insulin, and 1 mmol/L dexamethasone (all reagents from Sigma Aldrich). Lipid droplets were visualized by staining with oil red O staining (Sigma Aldrich). The percent of adipocytes was estimated by counting 500 total cells in multiple fields. The osteogenic differentiation was stimulated in a 3-week culture in media supplemented with 10% FBS, $10^{-7}$ mol/L dexamethasone, 10 mmol/L b-glycerol phosphate (Fluka, Buchs, Switzerland), and 100 mmol/L of L-ascorbic acid-2 phosphates. Assessment of calcium accumulation was visualized by von Kossa staining. For chondrogenesis differentiation, briefly cells were cultured in media supplemented with ITS+1 (Sigma Aldrich), 50 mmol/L L-ascorbic acid-2 phosphates (Sigma Aldrich), 55 mmol/L sodium pyruvate (Invitrogen), 25 mmol/L L-proline (Sigma Aldrich), and 10 ng/mL of transforming growth factor-beta (TGF-b) (Sigma Aldrich). Assessment of proteoglycan accumulation was visualized by alcian blue staining (Sigma Adrich). Adipogenic differentiation was confirmed by the accumulation of neutral lipid vacuoles. Osteogenic differentiation was confirmed in WJSCs by the deposition of a silver-stained mineralized matrix. Chondrogenic differentiation was confirmed by the formation of spheres in the micromass culture and the secretion of cartilage-specific proteoglycans stainable. WJSCs demonstrated a cartilage-like phenotype with chondrocyte-like lacunae (refer FIG. 5).

Example 10

Figure 6:
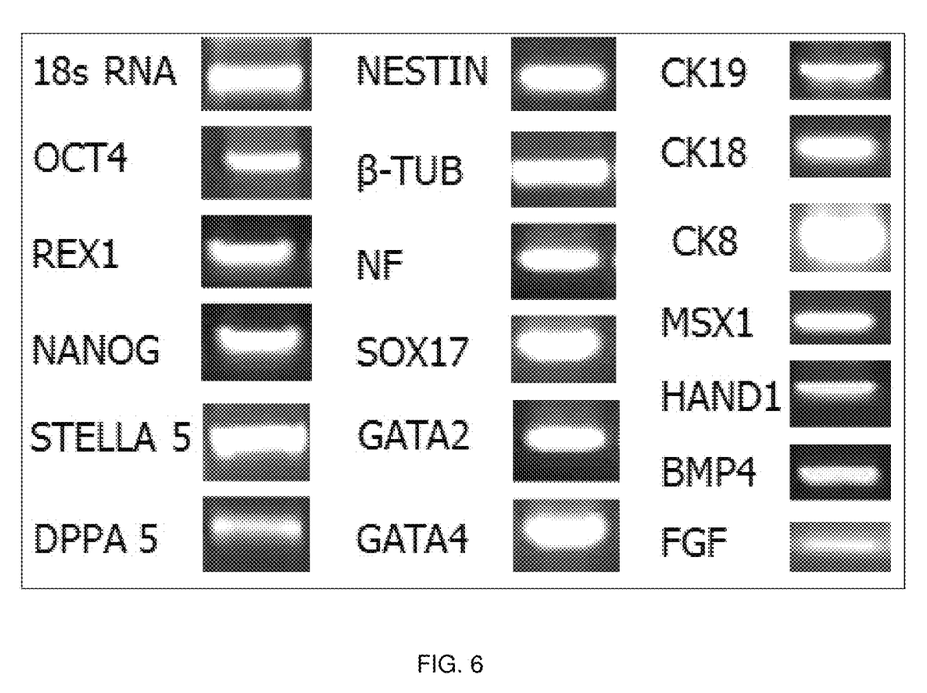
FIG. 6 illustrates the gene expression profiling of WJ-MSCs.

Gene Expression Profile of WJ-MSCs at Subculture 2 which is Also Known as Finished Product Total RNA was extracted by from WJ-MSCs at SC2 culture using Trizol (Invitrogen) according to the manufacturer's instructions. The RNA was reverse-transcribed into cDNA by using Superscript II reverse transcriptase (Invitrogen) according to the manufacturer's instructions. cDNA amplification was performed in a thermocycler by using Taq polymerase supplied with KCl buffer and 1.5 mmol/L $MgCl_2$ (Invitrogen) at 94° C./1 min, 58° C./30 sec, 72° C./1 min. Polymerase chain reaction (PCR) products were resolved on 1.5% agarose (Invitrogen) gel run in 1× Tris borate-ethylenediaminetetraacetic acid buffer. WJMSCs express pluripotent genes OCT4, REX1, NANOG, STELLA5 and DPPA 5. The culture also express some ectoderm (NESTIN, β-TUB, NF), endoderm (SOX17, GATA2, CK19, CK18, CK8) and mesoderm (GATA4, MSX1, HAND1, BMP4) markers (refer FIG. 6).

Example 11

Figure 7:
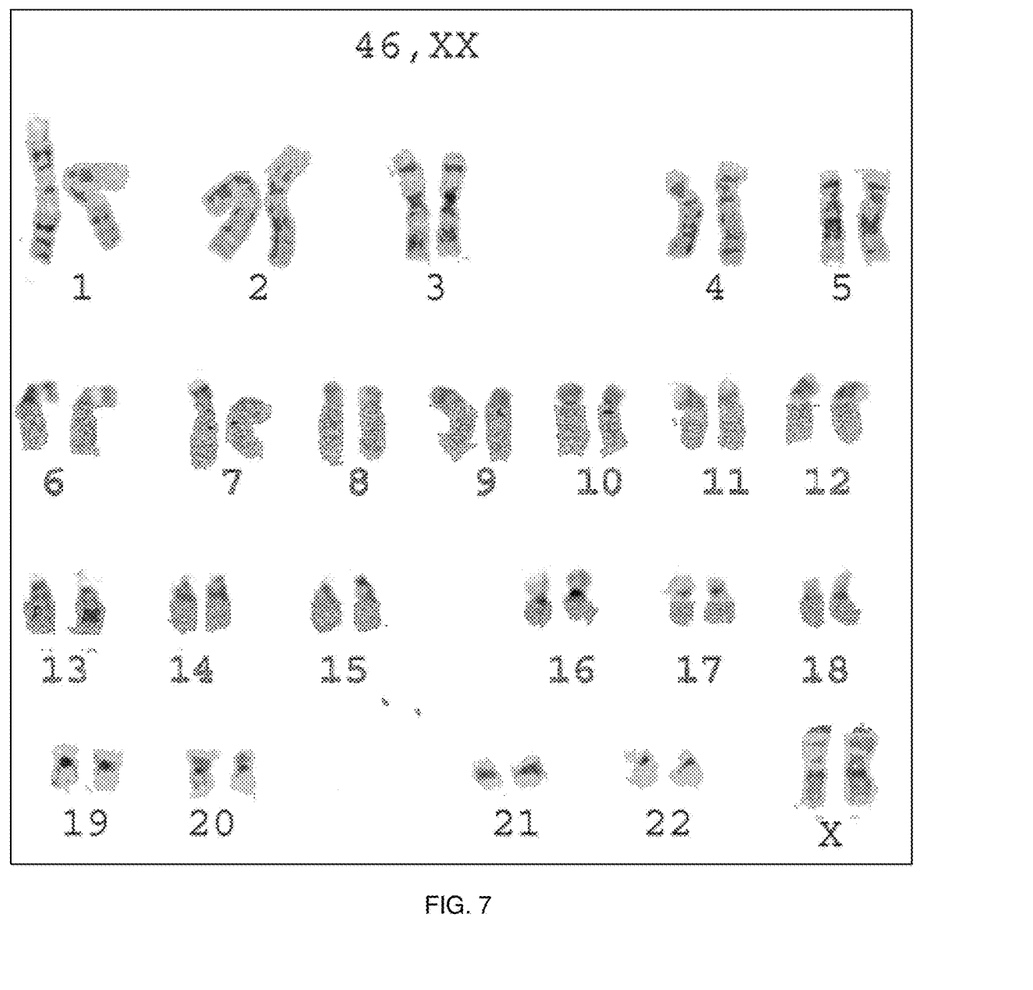
FIG. 7 illustrates the karyotype analysis of WJMSCs

Cytogenetic Stability of WJ-MSCs at Subculture 2 which is Also Known as Finished Product WJ-MSCs cultures were treated with colcemid 2 hours before harvest, detached by trysinization, and treated with 0.5 mol/L hypotonic solution (KCl/water) before fixing with Conroy's solution (3:1 methanol/glacial acetic acid). The spreads were treated with 0.005% trypsin, stained with Giemsa (Sigma Aldrich), and 20-30 separate metaphase spreads were examined for each culture. WJ-MSCs showed normal karyotypes at passage 2. A representative ideogram is illustrated in FIG. 7.

Example 12

Dopaminergic Neuron Differentiation of WJ-MSCs at Subculture 2 which is Also Known as Finished Product EB Formation (Hanging Drop Method) Stage 1, EB Formation At 80% confluency, WJMSCs were transferred into a non-adherent petri dish containing a neural-inducing medium (NIM) composed of 92% D-MEM/F-12 (1:1), 6000 mg/L D-glucose, 5% KnockOut SR, 2 mM L-glutamine, 1% MEM non-essential amino acids solution, 0.1 mM b-mercaptoethanol, and 1% N2 supplement (all from Gibco BRL). The EBs were well-developed under these conditions.

Dopa Media A

The cells were cultured on 200 mm cell culture dish (BD Pharmingen, San Diego, Calif.) in Neurobasal A media (GIBCO/Invitrogen, Carlsbad, Calif.) supplemented with B27 (Invitrogen, Carlsbad, Calif.), 20 ng/mL basic fibroblast growth factor (bFGF; Invitrogen) and 20 ng/mL epidermal growth factor (EGF; Invitrogen). Fresh culture medium including EGF and bFGF was added to the medium after 4-5 days of culture.

Dopa Media B

Figure 8:
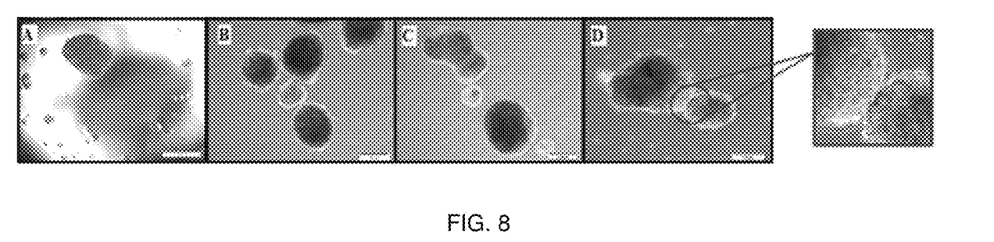
FIG. 8 illustrates the WJSCs cell aggregated derived from hanging drop method (A), EB formation in NIM (B), Neurosphere development in media A (C) and dopaminergic neuron differentiation in media B (D).

The cells were induced with a cocktail of 200 ng/mL sonic hedgehog (SHH), 100 ng/mL fibroblast growth factor 8 (FGF8), 10 ng/mL glial cell line-derived neurotrophic factor (GDNF; R&D Systems, Minneapolis, Minn.), and 10 μM forskolin (Sigma). Cells were then cultured at 37° C. with 5% CO 2 for 7 days. Half of the medium was replaced every 2-3 days. After 7 days of cultivation, the cells differentiated into neuronal cells and were tested for neural cell marker expression. WJ-MSCs cell aggregates derived from hanging drop method (FIG. 8A) formed embryonic bodies in NIM (FIG. 8B) and developed into neurosphere in media A (FIG. 8C) which expressed early neuronal markers (Nestin & β-tubulin). Further differentiation of neurospheres in media B expressed dopaminergic neuron specific markers (TH and GAD65&67) (refer FIG. 8).

Example 13

Figure 9:
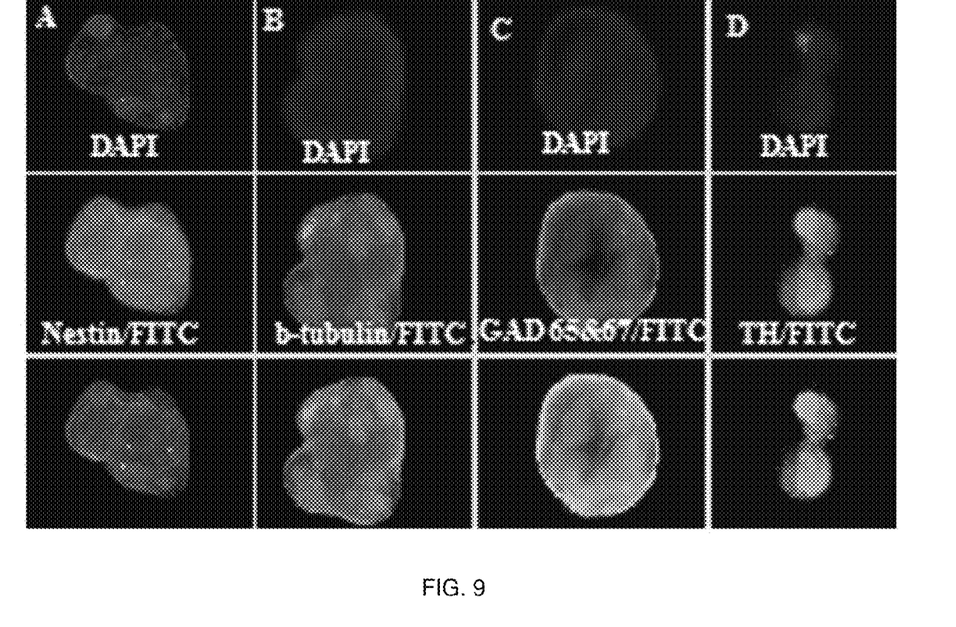
FIG. 9 illustrates the WJMSCs neurosphere (A and B) and dopaminergic neuron differentiated neurosphere (C and D).

Immunocytochemistry of WJ-MSCs at Subculture 2 which is Also Known as Finished Product Differentiated cells were fixed with 4% paraformaldehyde for 15 minutes at 25° C. and permeabilised using 0.1% Triton X-100 for 10 minutes at 25° C. Cells were then blocked with blocking buffer (DPBS containing 3% BSA) for 30 minutes at 25° C. and incubated overnight with primary antibodies at 1:500 dilution at 4° C. Primary antibodies used were Nestin-Ms, β-tubulin-Ms, GAD 65&67-Rb and TH-Rb (Abcam®). After three washes with DPBS, cells were incubated with secondary antibodies FITC-conjugated anti-rabbit IgG antibodies (A11012, Molecular probes) and FITC-conjugated anti-mouse IgG antibodies (ab6785, Abcam®). Nucleus was stained with anti-fade 4',6'-diamidino-2-phenylindole dihydrochloride (DAPI; Chemicon). Observations were made using a fluorescence microscope. Immunochemistry staining for WJMSCs derived neurospheres were positive for nestin and β-tubulin (FIGS. 9 A and B) whereas dopaminergic neuron differentiated neurosphere were positive for GAD 65&67 and TH (FIGS. 9 C and D).

The invention claimed is:

1. A method for proliferating viable cells from Wharton's jelly, wherein the method comprises the following steps:
    a) disinfecting an umbilical cord by cutting into pieces, removing blood contaminant by multiple washings with double distilled water and repeatedly immersing the washed umbilical cord pieces into Dulbecco's Phosphate Buffered Saline (DPBS) containing 20% Antibiotic-Antimycotic and 20% Penicillin-Streptomycin (Pen-Strep); then
    b) washing the umbilical cord pieces multiple times with double distilled water containing 1% Antibiotic-Antimycotic, and 1% Pen-Strep with additionally injecting heparin into the blood vessels and removing blood vessels from each umbilical cord piece;
    c) further disinfecting each umbilical cord piece by immersing into 70% ethanol for 30 seconds followed by immediately repeated immersions into double distilled water multiple times for 30 seconds per immersion:
    d) transferring the umbilical cord pieces into DPBS containing 5% Antibiotic-Antimycotic and incubating at 37° C. overnight and next day washing with the DPBS containing 5% Antibiotic-Antimycotic three times with 2 minutes incubation to provide processed umbilical cord tissue;
    e) preparing a primary stock culture using viable cells from Wharton's jelly, the viable cells being isolated from the processed umbilical cord tissue obtained from step (d); and
    f) proliferating the primary stock culture from step (e) in a Wharton's Jelly Complete Culture Medium (CCM) comprising 73% Knockout-Dulbecco's Modified Eagle Medium (KO-DMEM), 20% Fetal Bovine Serum (FBS), 200 units mL$^{-1}$/200 μg mL$^{-1}$ Pen-Strep, 10,000 units mL$^{-1}$/25 μg mL$^{-1}$ antibiotic-antimycotic, and 2% Glutamax;
    g) obtaining sub-cultured stocks from proliferated primary stock culture from step (f);
    h) harvesting viable cells from the sub-cultured stocks from step (g); and
    i) cryo-preserving viable Wharton's jelly mesenchymal stem cells (WJ-MSCs) from step (h) comprising more than 90% of the viable cells having CD44, CD73, CD90 phenotype, 70.4% having CD166 phenotype and also expressing pluripotent genes OCT4, REX1, NANOG, STELLA5 and DPPA, ectoderm gene markers NESTIN, P-TUB, and NF, endoderm gene markers SOX17, GATA2, CK19, CK18, and CK8, and mesoderm gene markers GATA4, MSX1, HAND1, and BMP4.

2. The method as claimed in claim 1 wherein the method step of preparing the primary stock culture comprises steps of:
    a) incubating the umbilical cord tissue in a mixture of Collagenase Type-IV Stock Solution and Knockout-Dulbecco's Modified Eagle Medium at 37° C. in 5% humidified carbon dioxide incubator;
    b) mincing the umbilical cord tissue from step (a) to obtain a desired size of about 2 mm$^3$ ;
    c) digesting the umbilical cord tissue from step (b) using trypsin-EDTA;
    d) diluting the digested umbilical cord tissue from step (c) with neutralization medium containing 95% KO-DMEM and 5% FBS;
    e) centrifuging the diluted mixture from step (d) to obtain a pellet of cells at 1800 rpm and temperature of (18° C. ±2° C.) for 5 minutes;
    f) re-suspending the pellet from step (e) in a fresh Wharton's jelly complete culture medium; and
    g) culturing cells from the pellet at 37° C. in 5% humidified carbon dioxide incubator until the confluency of the cells reaches between 80% and 85%.

3. The method as claimed in claim 1 wherein the method step of obtaining sub-cultured stocks comprises steps of:
    a) removing conditioned media from the primary stock culture;
    b) rinsing the stock culture from step (a) with Dulbecco's Phosphate Buffered Saline (DPBS);

c) trypsinizing the stock culture with Trypsin-EDTA;
d) adding the Wharton's jelly complete culture medium into the stock culture from step (c) to obtain cell suspension;
e) centrifuging the cell suspension from step (d) at 1500 rpm and temperature of (18° C.±2° C.) for 10 minutes to obtain a pellet of cells;
f) re-suspending the pellet from step (e) with fresh Wharton's jelly complete culture medium; and
g) culturing cells from the pellet at 37° C. in 5% humidified carbon dioxide incubator until the confluency of the cells reaches between 80% and 85%.

* * * * *